United States Patent
Ishioka et al.

(10) Patent No.: US 11,276,506 B2
(45) Date of Patent: Mar. 15, 2022

(54) PRODUCING METHOD OF RADIOISOTOPE AND RADIOISOTOPE PRODUCING APPARATUS

(71) Applicant: NATIONAL INSTITUTES FOR QUANTUM SCIENCE AND TECHNOLOGY, Chiba (JP)

(72) Inventors: Noriko Ishioka, Gunma (JP); Hiroo Kondo, Aomori (JP); Shigeki Watanabe, Gunma (JP)

(73) Assignee: NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 0 days.

(21) Appl. No.: 16/649,685

(22) PCT Filed: Oct. 30, 2018

(86) PCT No.: PCT/JP2018/040359
§ 371 (c)(1),
(2) Date: Mar. 23, 2020

(87) PCT Pub. No.: WO2019/088113
PCT Pub. Date: May 9, 2019

(65) Prior Publication Data
US 2020/0321138 A1    Oct. 8, 2020

(30) Foreign Application Priority Data
Oct. 31, 2017 (JP) .............................. JP2017-210442

(51) Int. Cl.
*G21G 1/00* (2006.01)
*G21G 1/10* (2006.01)
(Continued)

(52) U.S. Cl.
CPC .............. *G21G 1/001* (2013.01); *G21G 1/10* (2013.01); *G21K 5/08* (2013.01); *A61N 5/10* (2013.01); *G21G 2001/0094* (2013.01)

(58) Field of Classification Search
CPC ... G21G 2001/0089; G21G 2001/0084; G21G 1/00; G21G 1/0005; G21G 1/001;
(Continued)

(56) References Cited

U.S. PATENT DOCUMENTS 3,833,469 A * 9/1974 Robson ................ C01G 99/006
424/1.61
5,802,439 A * 9/1998 Bennett .................... G21G 1/12
376/186
(Continued)

FOREIGN PATENT DOCUMENTS

| JP | 2010-164477 | 7/2010 |
| JP | 2016-80574 | 5/2016 |
| WO | WO-2017/135196 A1 | 8/2017 |

OTHER PUBLICATIONS

Tall et al., "Volatile Elements Production Rates in a Protein-irradiated Molten Lead-bismuth Target", International Conference on Nuclear Data for Science and Technology, Article No. 281, Mar. 21, 2008, pp. 1069-1072.
(Continued)

*Primary Examiner* — Darlene M Ritchie
(74) *Attorney, Agent, or Firm* — Marshall, Gerstein & Borun LLP

(57) ABSTRACT

There is provided a method of producing a radioisotope with a production time shortened. There is provided a producing method of a radioisotope, the method including: irradiating a target substance with a radiation beam; and extracting the radioisotope which is generated by irradiating the target
(Continued)

substance and flowing a gas over the substance to transport the radioisotope in gas phase toward an outlet.

19 Claims, 4 Drawing Sheets

(51) Int. Cl.
  *G21K 5/08* (2006.01)
  *A61N 5/10* (2006.01)
(58) Field of Classification Search
  CPC .. G21G 1/10; G21G 1/06; G21G 1/08; G21G 1/04; G21G 1/12; G21G 4/00; G21G 4/04; G21G 4/06; G21G 4/08; A61N 5/10; A61N 5/022; A61N 5/00; A61N 2005/1019; A61N 2005/1022; G21K 5/04; G21K 5/08
  See application file for complete search history.

(56) References Cited

U.S. PATENT DOCUMENTS

| | | | | |
|---|---|---|---|---|
| 6,157,036 | A * | 12/2000 | Whiting | G21G 1/0005 |
| | | | | 250/432 PD |
| 2008/0137791 | A1 * | 6/2008 | Sumini | G21G 1/04 |
| | | | | 376/126 |
| 2009/0060812 | A1 * | 3/2009 | Schenter | G21G 1/10 |
| | | | | 423/249 |
| 2009/0162278 | A1 * | 6/2009 | Ravn | G21G 1/001 |
| | | | | 424/1.37 |
| 2011/0305309 | A1 * | 12/2011 | Brown | G21G 1/00 |
| | | | | 376/189 |
| 2016/0023182 | A1 * | 1/2016 | Tadokoro | G21G 1/10 |
| | | | | 204/157.44 |
| 2016/0035448 | A1 | 2/2016 | Siclovan et al. | |
| 2017/0323696 | A1 | 11/2017 | Kani et al. | |
| 2019/0043631 | A1 | 2/2019 | Matsuzaki et al. | |
| 2019/0311819 | A1 * | 10/2019 | Henriksen | G21G 1/10 |

OTHER PUBLICATIONS

Watanabe et al., "Development of a Novel Large-scale Production Method of At-211 in TIARA", QST Takasaki Advanced Radiation Research Institute.
Gagnon et al., "Design and Evaluation of an External High-current Target for Production of $^{211}$At", Journal of Labelled Compounds and Radiopharmaceuticals, Oct. 17, 2012, 5 pages.
Nagatsu et al., "Production of $^{211}$At by a Vertical Beam Irradiation Method", Applied Radiation and Isotopes 94, 2014, pp. 363-371.
Search Report in International Application No. PCT/JP2018/040359 dated Dec. 4, 2018, 3 pages.
International Preliminary Report on Patentability and Written Opinion in International Application No. PCT/JP2018/040359 dated May 5, 2020, 9 pages.
Extended European Search Report in EP Application No. 18873625.0 dated Jul. 9, 2021, 7 pages.

* cited by examiner

FIG. 3

| | GROUP 14 | | GROUP 15 | | GROUP 16 | | GROUP 17 | |
|---|---|---|---|---|---|---|---|---|
| | Ge | | As | | Se | | Br | |
| Pressure | Temp | | Temp | | Temp | | Temp | |
| Pa | °C | K | °C | K | °C | K | °C | K |
| 1.0.E+00 | 1371 | 1644 | 280 | 553 | 227 | 500 | -88 | 185 |
| 1.0.E+01 | 1541 | 1814 | 323 | 596 | 279 | 552 | -72 | 201 |
| 1.0.E+02 | 1750 | 2023 | 373 | 646 | 344 | 617 | -53 | 220 |
| 1.0.E+03 | 2014 | 2287 | 433 | 706 | 431 | 704 | -29 | 244 |
| 1.0.E+04 | 2360 | 2633 | 508 | 781 | 540 | 813 | 3 | 276 |
| 1.0.E+05 | 2741 | 3014 | 601 | 874 | 685 | 958 | 59 | 332 |
| | Sn | | Sb | | Te | | I | |
| Pressure | Temp | | Temp | | Temp | | Temp | |
| Pa | °C | K | °C | K | °C | K | °C | K |
| 1.0.E+00 | 1224 | 1497 | 534 | 807 | | | -13 | 260 |
| 1.0.E+01 | 1384 | 1657 | 603 | 876 | | | 9 | 282 |
| 1.0.E+02 | 1582 | 1855 | 738 | 1011 | | | 36 | 309 |
| 1.0.E+03 | 1834 | 2107 | 946 | 1219 | | | 69 | 342 |
| 1.0.E+04 | 2165 | 2438 | 1218 | 1491 | 769 | 1042 | 108 | 381 |
| 1.0.E+05 | 2620 | 2893 | 1585 | 1858 | 993 | 1266 | 184 | 457 |
| | Pb | | Bi | | Po | | At | |
| Pressure | Temp | | Temp | | Temp | | Temp | |
| Pa | °C | K | °C | K | °C | K | °C | K |
| 1.0E+00 | 705 | 978 | 668 | 941 | | | 88 | 361 |
| 1.0E+01 | 815 | 1088 | 768 | 1041 | | | 119 | 392 |
| 1.0E+02 | 956 | 1229 | 892 | 1165 | | | 156 | 429 |
| 1.0E+03 | 1139 | 1412 | 1052 | 1325 | 573 | 846 | 202 | 475 |
| 1.0E+04 | 1387 | 1660 | 1265 | 1538 | 730 | 1003 | 258 | 531 |
| 1.0E+05 | 1754 | 2027 | 1562 | 1835 | 963 | 1236 | 334 | 607 |

PRODUCING METHOD OF RADIOISOTOPE AND RADIOISOTOPE PRODUCING APPARATUS

TECHNICAL FIELD

The present invention relates to a producing method of a radioisotope, and a radioisotope producing apparatus.

BACKGROUND ART

Examples of treatment methods of cancer include resection, administration of anticancer agents, and external radiation exposure. Many lives are still being lost due to cancers which even those techniques are difficult to cure. Accordingly, to develop novel treatment methods is a worldwide urgent problem.

Astatine 211 ($^{211}$At) is a radioisotope (RI) emitting α-beams which kill cells, and leads to high expectations as next-generation cancer therapy drugs which are administrated into the body. Europe and America are leading studies on $^{211}$At into drugs, but in production of $^{211}$At which is the backbone of those, do not handle its supply in an amount (tens of gigabecquerels) of radioactivity with which a plurality of hospitals can perform medical treatments.

DOCUMENTS OF PRIOR ARTS

Non Patent Document

[Non Patent Document 1] Shigeki Watanabe, Noriko Ishioka, et al., "Development of a novel large-scale production method of At-211 in TIARA", the 16th Radiation Process Symposium, November, 2016, Tokyo

[Non Patent Document 2] K. Gagnon, et al., "Design and evaluation of an external high-current target for production of 211At", Label. Compd. Radiopharm 2012, 55 436-440

[Non Patent Document 3] Kotaro Nagatsu, et al., "Production of $^{211}$At by a vertical beam irradiation method", Applied Radiation and Isotopes, 2014, 94, 363-371

SUMMARY OF THE INVENTION

Problems to be Solved by the Invention

Conventionally, a radioisotope has been generated in a solid metal by irradiating a radiation on the solid metal as a target, and then, the solid metal after irradiation of the radiation has been taken out to separately collect the RI. It is a relatively unignorable problem in such irradiation with a solid metal being as a target in the field of production of medical RI to secure soundness of the target in irradiation since damage to (melting of) the target in irradiation disturbs efficient generation of an RI, and in addition, causes a concern that the generated RI is released. In addition to this, while medical sites want developments of techniques capable of quickly affording target RIs after irradiation, there has not been a successful example yet in irradiation with a metal being as a target.

The aforementioned problem is significant in production of $^{211}$At. $^{211}$At is generated by irradiating alpha- (α-)rays on bismuth (Bi), Bi has an especially low melting point as a target, and this limits irradiation power, which problematically disturbs its large-scale production. Accordingly, irradiation schemes have been developed such that Bi does not melt. Moreover, in a conventional dry distillation and separation procedure in which irradiated solid Bi is heated to be separated using the difference in saturated vapor pressure between $^{211}$At and Bi, it takes time to take out the solid Bi and separate and purify $^{211}$At, which has problematically caused a decay loss of $^{211}$At with approximately seven hours of half-life.

As above, in RI production with a solid being as a target, there have had to be taken a series of procedures of irradiation, taking-out of the target, and separation and purification of a target RI from the target.

An object of the present invention is to provide a method of producing a radioisotope with a production time shortened.

Means for Solving the Problems

In order to solve the aforementioned problem, the following means is employed.

Namely, a first aspect is a producing method of a radioisotope, the method including:

irradiating a radiation beam on a target substance; and extracting the radioisotope which is generated by irradiating the radiation beam and transferred to gas from the gas.

Effects of the Invention

According to the present invention, there can be provided a method of producing a radioisotope with a production time shortened.

BRIEF DESCRIPTION OF THE DRAWINGS

FIG. 3 is a table exemplarily presenting relation between saturated vapor pressures and temperatures of group 14, group 15, group 16 and group 17 elements.

MODE FOR CARRYING OUT THE INVENTION

Hereafter, an embodiment is described with reference to the drawings. The configuration of the embodiment is exemplary, and the configuration of the invention is not limited to the specific configuration of the embodiment of the disclosure. When implementing the invention, a specific configuration according to the embodiment may be properly employed.

Embodiment

Exemplary Configuration

Figure 1:
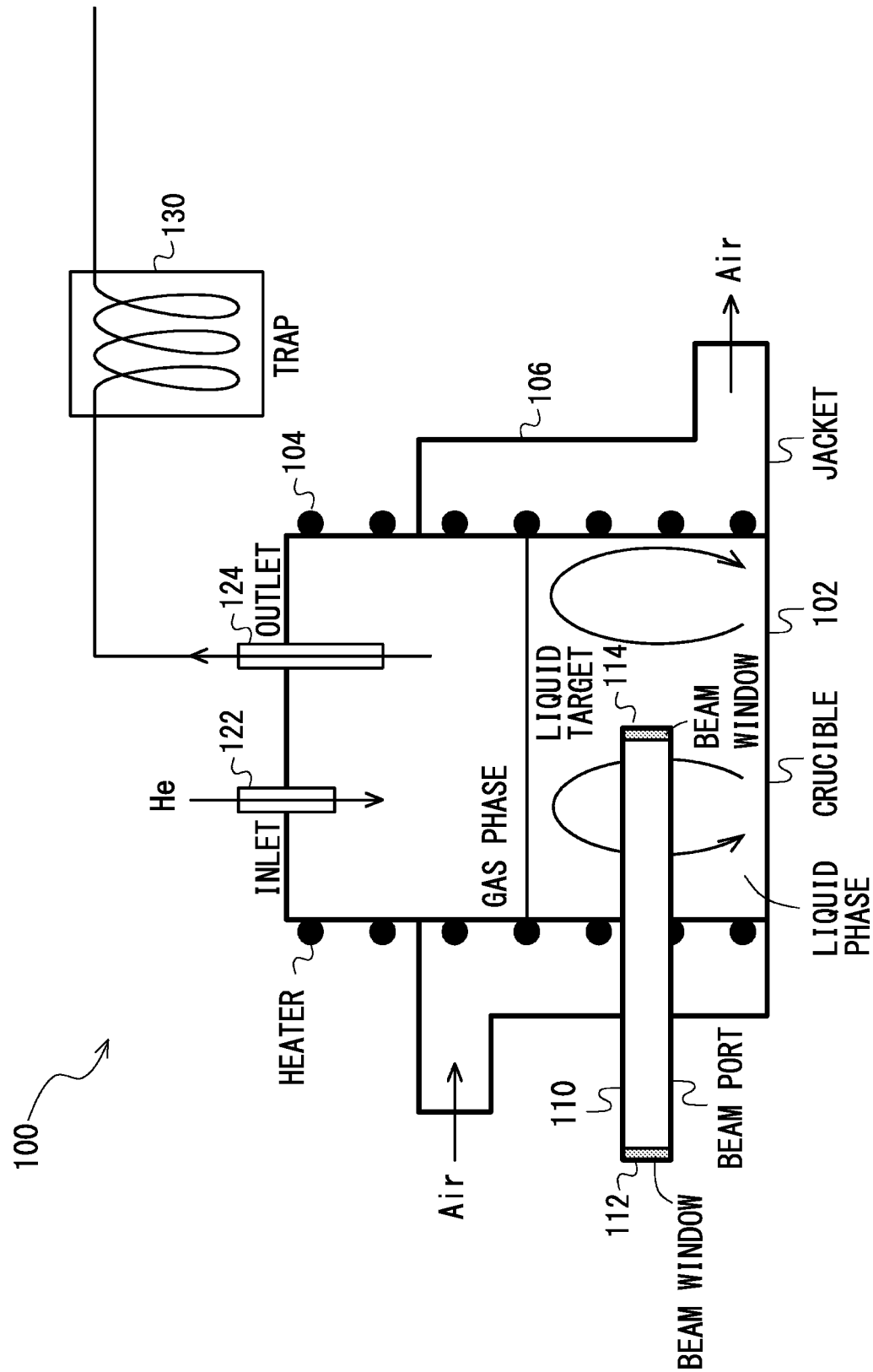
FIG. 1 is a diagram illustrating an exemplary configuration of a radioisotope producing apparatus of an embodiment.

FIG. 1 is a diagram illustrating an exemplary configuration of a radioisotope producing apparatus of the present embodiment. A radioisotope producing apparatus 100 includes a crucible 102, a heater 104, a jacket 106, a beam port 110, a beam window 112, a beam window 114, an inlet 122, an outlet 124 and a trap 130.

The crucible 102 is a heat-resistant vessel in which a substance as a target (for example, bismuth) is molten. The crucible 102 is a container which houses the substance as the target. As the crucible 102, for example, quartz, china and porcelain, metal, and the like are used. For the crucible 102, it is expected that it is at least durable against the temperature at the melting point of the substance as the target. While the crucible 102 is hermetically sealed, gas can pass through the inlet 122 and the outlet 124 between the inside and the outside. The beam port 110 is connected to the crucible 102. The crucible 102 is exemplarily a heat-resistant vessel.

The heater 104 is heating means for heating the crucible 102. The heater 104 heats the crucible 102, and thereby, heats the substance as the target in the crucible 102. Thereby, the target substance can be promoted to be molten. Typically, it melts and liquefies the target substance. As the heater 104, for example, a micro-sheath heater is used. The heater 104 is not limited to a micro-sheath heater. All the substance as the target in the crucible 102 is not needed to be liquefied. Namely, a part of the substance as the target may be still solid. When the substance as the target is heated by the heater 104, the relevant substance is liquefied. A liquid phase of the liquefied substance and a gas phase of gas introduced from the inlet 122 and the like exist in the crucible 102. The heater 104 is exemplarily a heating unit.

Notably, while there is herein exemplarily described the case where the heater 104 heats the target substance to liquefy the relevant substance, the heating means is not limited to this. For example, temperature increase at a beam irradiated portion at which a radiation beam is irradiated on the target substance (temperature increase originated from heat due to nuclear reaction) may be used. Two or more conventionally known items of heating means may be combined, and, for example, both the aforementioned heating with the heater 104 and the temperature increase originated from radiation beam irradiation may be used.

The jacket 106 is a cooling space arranged around the crucible 102. An introduction port and a discharge port for a cooling material (for example, air) are provided on the jacket 106, and the cooling material is introduced into the jacket 106 from the introduction port to cool the crucible 102. Cooling is also performed by suspending heating of the heater 104, and the cooling is more quickly performed by introducing the cooling material into the jacket 106. The cooling material introduced into the jacket 106 is not limited to air (for example, the air at ambient temperature) but may be other gas such as nitrogen or liquid such as water.

While there is herein exemplarily described the case where the cooling material is introduced into the jacket 106 to cool the crucible 102 as a cooling method of the crucible 102, not limited to this, one or two or more conventionally known items of cooling means can be combined and employed. For example, an element such as a Peltier element may be used.

The beam port 110 is a passage for introducing a radiation beam irradiated on the substance as the target in the crucible 102. The interior of the beam port 110 is evacuated to a vacuum, or gas (for example, He gas or the like) is introduced thereinto. The beam port 110 is tubular, and both ends are closed by the beam window 112 and the beam window 114. It connects to a radiation beam generator such as an accelerator with the beam window 112. The beam window 112 and the beam window 114 are, for example, metal plates. A radiation beam accelerated by an accelerator or the like included in the radiation beam generator enters the beam port 110 from the beam window 112, passes through the beam window 114, and is irradiated inside the crucible 102. Namely, it is irradiated on a target (typically, a liquefied liquid target). The beam window 112 and the beam window 114 are substances which at least part of the radiation beam can pass through. Moreover, the beam window 114 is a substance which is not molten even at the temperature of the liquid target in the crucible 102. The beam port 110, the beam window 112 and the beam window 114 are exemplarily a beam introducing portion.

The inlet 122 is an introduction port for introducing gas into the crucible 102. The inlet 122 is, for example, a tubular pipe. The inlet 122 connects the inside and the outside of the crucible 102 such that gas can pass through therebetween. Gas for collecting a radioisotope is introduced from the inlet 122. As such gas, gas that is not liquefied or solidified by cooling with the trap 130 mentioned later is preferably employed. The relevant gas is, for example, He gas. Gas is introduced from the inlet 122, and thereby, the gas is discharged from the outlet 124. As a result, in the gas phase inside the crucible 102, a flow of the gas from the inlet 122 toward the outlet 124 arises. Such flow of the gas can carry the radioisotope transferred to the gas phase in the outlet direction. The amount of gas discharged from the outlet 124 can be regulated by regulating the amount of the gas introduced from the inlet 122. Moreover, the pressure of the gas phase in the crucible 102 can be controlled by regulating the amount of the introduced gas by regulating the amount of the gas discharged from the outlet 124 (for example, decreasing the flow rate, typically, closing the outlet 124) or by closing the discharge side of the trap 130 or by the similar manner. The pressure of the gas phase in the crucible 102 can be more accurately controlled by combining regulating the gas amount discharged from the outlet 124 or regulating the gas amount discharged from the discharge side of the trap 130 to regulating the gas amount introduced from the inlet 122.

The outlet 124 is a discharge port for discharging gas from the crucible 102. The outlet 124 is, for example, a tubular pipe. The outlet 124 connects the inside of the crucible 102 and the trap 130 such that gas can pass through therebetween. The gas introduced from the inlet 122 and a gasified radioisotope and the like are discharged from the outlet 124. The radioisotope is a substance generated by irradiating the radiation beam on the liquid target.

The trap 130 is a device that separates and extracts the radioisotope from the gas introduced from the crucible 102. The trap 130 is hermetically connected to the crucible 102 such that gas containing the radioisotope can pass through. For example, the trap 130 cools gas introduced from the crucible 102. Thereby, it can liquefy or solidify the radioisotope to separate the radioisotope from the gas containing the radioisotope (typically, mixture gas with He). The aforementioned cooling is not specially limited as long as the radioisotope can be separated from the mixture gas, but may be performed, for example, at a temperature not more than the boiling point of the radioisotope, preferably at a temperature not more than the melting point of the radioisotope or at a temperature not more than the freezing point thereof. It is still preferably set to be a temperature lower than the melting point and the freezing point of the radioisotope. For example, it can be 4° C. (277 K) or less, typically −10° C. (263 K) or less, preferably −80° C. (193 K) or less, still preferably −196° C. (77 K) or less. As cooling means, for example, cooling water, acetone-dry ice, liquid nitrogen, or the like can be used. At that time, since He gas is not liquefied or solidified at the liquid nitrogen temperature (77 K), the radioisotope can be separated. Moreover, gas that is discharged from the trap 130 after the separation (for example, He gas) may be reintroduced into the crucible 102 from the inlet 122. In the trap 130, the radioisotope can be separated by a similar method to known dry distillation and separation. The trap 130 is exemplarily an extracting unit.

One or more items of temperature measuring means such as thermocouples may be installed in the crucible 102. With the temperature measuring means, the temperature at a liquid phase position and the temperature at a gas phase position in the crucible 102 can be measured. For example, it can be determined whether or not the substance as the target is liquefied by measuring the temperature at the liquid phase position.

(Exemplary Operation)

Figure 2:
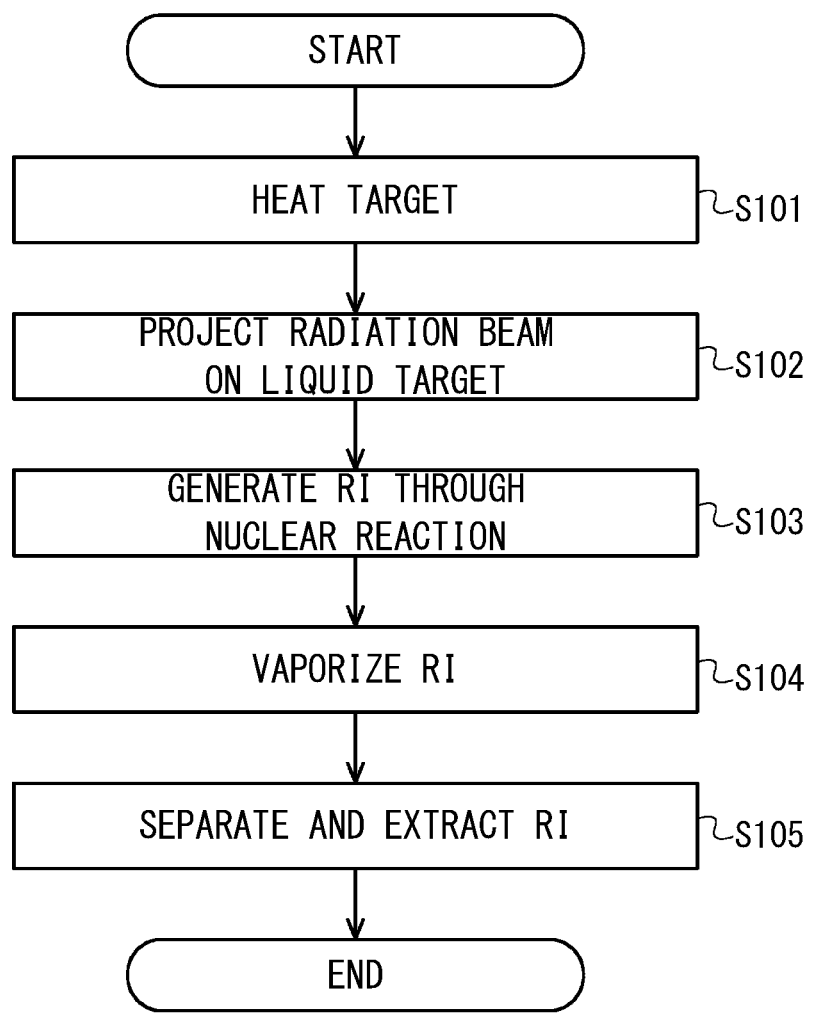
FIG. 2 is a diagram exemplarily illustrating an operation flow of a radioisotope producing apparatus.

FIG. 2 is a diagram exemplarily illustrating an operation flow of a radioisotope producing apparatus. It is herein supposed that the substance as the target has been already put in the crucible 102. Moreover, it is supposed that He gas is being introduced from the inlet 122 at a predetermined amount per unit time.

In S101, the heater 104 of the radioisotope producing apparatus 100 heats the crucible 102. The heater 104 may be controlled, for example, by a control device such as a computer or the like. The crucible 102 is heated, and thereby, the substance as the target in the crucible 102 is heated (typically, to be molten into liquid). The crucible 102 is preferably heated at a temperature not less than the melting point of the substance as the target. The liquefied substance as the target is also called liquid target. The substance as the target is herein supposed to be bismuth (Bi). The substance as the target is, for example, a group 14, group 15 or group 16 element in the periodic table. Since the melting point of bismuth is 271° C., the crucible 102 may be heated at 271° C. or more. The crucible 102 is herein supposed to be heated at 300° C. by the heater 104. The temperature of the target (liquid target) is preferably a temperature at which a ratio of the saturated vapor pressure of the generated radioisotope relative to the saturated vapor pressure of the liquid target is higher. Moreover, in order to efficiently obtain the target radioisotope, a target element is preferably selected with which a ratio of the saturated vapor pressure of the generated radioisotope relative to the saturated vapor pressure of the liquid target is higher. In this stage, the type of a irradiated radiation beam is selected as follows.

In S102, a radiation beam irradiates on the liquid target in the crucible 102 via the beam port 110. The radiation of the radiation beam is, for example, α-beams ($^4He^{2+}$), $^3He^{2+}$, $^1H^+$, $^2H^+$, $^7Li^{3+}$, or the like. The radiation beam is herein supposed to be α-beams. When the substance as the target is a group 13, group 14, group 15 or group 16 element, it is $^1H^+$, $^2H^+$, $^4He^{2+}$, $^3He^{2+}$, or $^7Li^{3+}$. Thereby, a main radioisotope generated through nuclear reaction between the substance as the target and the radiation beam becomes a group 15, group 16, group 17 or group 18 element. Moreover, the element of the target is preferably a metal.

In S103, the radioisotope is generated through nuclear reaction between the substance as the target and the radiation beam. When the substance as the target is Bi and the radiation beam is α-beams, a mainly generated radioisotope is $^{211}At$. Moreover, in the liquid phase of the crucible 102, Bi heated with heat due to the nuclear reaction rises, Bi cooled with gas in the gas phase and air or the like via the wall of the crucible 102 falls, and thereby, a convection current of Bi arises. Therefore, the temperature of Bi in the liquid phase can be held to be constant.

In S104, the radioisotope generated by irradiating the radiation beam is vaporized. For example, the saturated vapor pressure at the melting point (302° C.) of At is $4\times10^4$ Pa. Generated At is vaporized until a partial pressure of At in the crucible 102 becomes the saturated vapor pressure. Moreover, the saturated vapor pressure at the melting point (271° C.) of Bi is $1.6\times10^{-5}$ Pa. Bi is also vaporized until a partial pressure of Bi in the crucible 102 becomes the saturated vapor pressure. When it is supposed that the saturated vapor pressure of At at the melting point (271° C.) of Bi is approximately the same as the saturated vapor pressure of At at its melting point (302° C.), the saturated vapor pressure of At is $10^9$ times or more higher than the saturated vapor pressure of Bi. Accordingly, even when the ratio of At relative to Bi is very low in the liquid phase of the crucible 102, most of elements vaporized from the liquid surface (elements transferred from the liquid phase to the gas phase) is At since the partial pressure of Bi immediately reaches its saturated vapor pressure in the gas phase. For example, when the temperature of the liquid target is 300° C., a ratio of At out of the elements vaporized from the liquid surface is 99% or more if the volume of Bi is appropriately set. Namely, the elements vaporized from the liquid surface is almost At. The amount of At existing in the gas phase is much larger than the amount of Bi existing in the gas phase. Therefore, At is separated from Bi.

Namely, when the saturated vapor pressure of the element generated by irradiation is higher than the saturated vapor pressure of the element as the target, most of elements vaporized from the liquid surface of the liquid phase are to be the generated element (radioisotope). By irradiating the radiation beam on an element as the target, the radioisotope is generated and transferred to the gas phase (gas).

FIG. 3 is a table exemplarily presenting relation between saturated vapor pressures and temperatures of group 14, group 15, group 16 and group 17 elements. For example, the saturated vapor pressure of group 14 Ge at 2014° C. is $10^3$ Pa. It is known in principle that the saturated vapor pressure of an element monotonically increases with respect to its temperature. Herein, saturated vapor pressures are compared between elements in the same period. In the table of FIG. 3, as to the same saturated vapor pressure, the temperatures of group 14, group 15 and group 16 elements are higher than the temperature of group 17 one. Namely, in comparison for the same temperatures, the saturated vapor pressures of the group 14, group 15 and group 16 elements are lower than the saturated vapor pressure of the group 17 element. Moreover, the boiling point of a group 18 element is generally much lower than the boiling points of the other elements. Therefore, in comparison for the same temperatures, the saturated vapor pressures of the group 14, group 15 and group 16 elements are lower than the saturated vapor pressure of the group 18 element. Namely, the saturated vapor pressures of the group 14, group 15 and group 16 elements at the melting points of the group 14, group 15 and group 16 elements are lower than the saturated vapor pressures of the group 17 and group 18 elements at the melting points of the group 14, group 15 and group 16 elements. Otherwise, the group 17 and group 18 elements are gas at the melting points of the group 14, group 15 and group 16 elements. Accordingly, a ratio of the radioisotope elements vaporized from the liquid surface is made high by setting the liquid target to be a group 14, group 15 or group 16 element and setting the generated element (radioisotope) to be a group 17 or group 18 element.

In S105, the radioisotope (for example, $^{211}$At) vaporized into the gas phase from the liquid surface of the liquid phase reaches the trap 130 via the outlet 124 along with He gas and the like in the gas phase. The trap 130 extracts the radioisotope by being cooled with liquid nitrogen or the like or by the similar manner. By cooling with liquid nitrogen, He gas is still gas in the trap 130 and passes therethrough, while the radioisotope remains in the trap 130 due to its solidification or the like. Thereby, the radioisotope can be separated and extracted.

With the radioisotope producing apparatus 100, separation and extraction of the radioisotope in the trap 130 can be performed while irradiation of the radiation beam being continued. Namely, with the radioisotope producing apparatus 100, irradiation of the radiation beam and extraction of the radioisotope can be performed in parallel. When irradiation of the radiation beam and extraction of the radioisotope are performed in parallel, any one process of irradiation of the radiation beam and extraction of the radioisotope may be suspended. The target element does not have to be taken out of the crucible 202 in extraction of the radioisotope. Therefore, the radioisotope producing apparatus 100 can efficiently generate the radioisotope.

(Modification)

Figure 4:
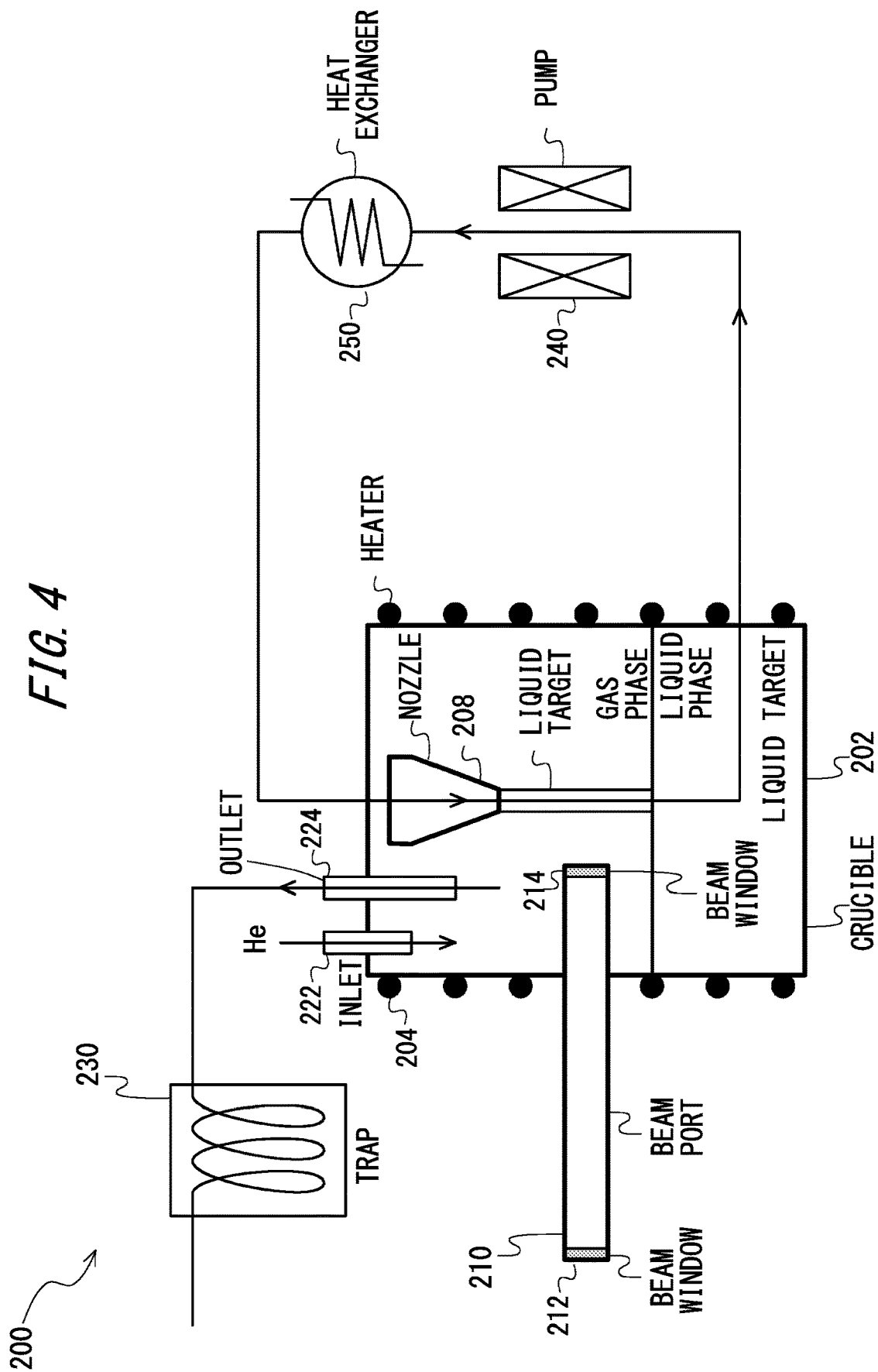
FIG. 4 is a diagram illustrating an exemplary configuration of a radioisotope producing apparatus of a modification of the embodiment.

FIG. 4 is a diagram illustrating an exemplary configuration of a radioisotope producing apparatus of a modification of the present embodiment. A radioisotope producing apparatus 200 in FIG. 4 includes a crucible 202, a heater 204, a nozzle 208, a beam port 210, a beam window 212, a beam window 214, an inlet 222, an outlet 224, a trap 230, a pump 240 and a heat exchanger 250. The radioisotope producing apparatus 200 may include a jacket which cools the crucible 202 similarly to the radioisotope producing apparatus 100 in FIG. 1.

The crucible 202, the heater 204, the beam port 210, the beam window 212, the beam window 214, the inlet 222, the outlet 224 and the trap 230 have the same configurations as those of the corresponding members in the radioisotope producing apparatus 100.

A passage for discharging the liquid target is provided in a lower portion of the liquid phase of the crucible 202, and the liquid target is discharged from the crucible 202 by the pump 240. The discharged liquid target is cooled by the heat exchanger 250. The cooled liquid target is introduced into the nozzle 208 disposed in an upper portion of the crucible 202. The liquid target introduced into the nozzle 208 flows like a waterfall from a lower portion of the nozzle 208, and reaches the liquid phase of the crucible 202. The beam port 210 is installed such that the radiation beam is irradiated on the liquid target that flows out of the nozzle 208. By forcibly circulating the liquid target, heat generated through nuclear reaction can be efficiently removed, and temperature increase in the crucible 202 can be suppressed.

The radioisotope producing apparatus 200 operates similarly to the radioisotope producing apparatus 100 except the portion which forcibly circulates the liquid target.

(Operation and Effects of Embodiment)

Conventionally, a radiation beam has been irradiated on a solid target put in an apparatus to generate a radioisotope in the solid target. Therefore, the solid target put in the apparatus has been taken out after the irradiation to extract the radioisotope by dry distillation and separation of heating, melting and other processing of the solid target. A time loss has arisen during the process from taking-out of the solid target to completion of the dry distillation and separation. Moreover, irradiation power has been wanted to be suppressed such that the solid target does not melt in irradiation on the solid target. Suppression of the power causes the amount of the generated radioisotope to decrease.

On the contrary, with the apparatus of the present embodiment, a radiation beam is irradiated on a liquid target to generate a radioisotope in the liquid target. By regulating the temperature and the pressure near the liquid surface of the liquid target, a ratio of the generated and vaporized radioisotope relative to the elements vaporized from the liquid phase can be made high. Since in the aforementioned example, the saturated vapor pressure of $^{211}$At is much higher than the saturated vapor pressure of Bi, most of elements vaporized from the liquid phase is $^{211}$At. Therefore, collecting the vaporized elements is to purify the radioisotope. The process of generation, separation and purification of the radioisotope spontaneously proceeds until the partial pressure of $^{211}$At near the liquid surface of the liquid target becomes the saturated vapor pressure to reach the equilibrium state. Accordingly, when At is being extracted continuously or in appropriate timing, $^{211}$At can continue to be produced continuously or intermittently. Moreover, with the apparatus of the present embodiment, since the radioisotope can be extracted without suspending irradiation of the radiation beam on the liquid target to take out the liquid target, production of the radioisotope from generation to extraction of the radioisotope can be performed in a short time. Namely, according to the apparatus of the present embodiment, the radioisotope can be extracted from gas containing the radioisotope generated and vaporized by irradiating the radiation beam.

Moreover, with the apparatus of the present embodiment, irradiation power is not wanted to be suppressed such that the target does not melt since the target is liquid, and the irradiation power of the radiation beam can be made high without increasing the temperature of the liquid target by a convection current, a forcible circulation and the like of the liquid target for cooling it. Such higher irradiation power can produce larger amount of radioisotopes.

Notably, while in the aforementioned embodiment and its modification, there are exemplarily described cases where the target substance is bismuth (Bi), the radiation beam irradiated on the target substance is α-beams, and thereby, $^{211}$At is generated as the radioisotope, in the aforementioned embodiment and its modification, the target substance may be a metal other than bismuth (Bi), a radiation beam other than α-beams may be irradiated on the target substance, and a radioisotope other than $^{211}$At may be generated.

The following tables are tables presenting combination patterns of target substances, radiation beams and radioisotopes which can be applied to the aforementioned embodiment and its modification.

TABLE 1

| No. | TARGET ATOMIC NUMBER | TARGET ELEMENT | MASS NUMBER | NUCLEAR REACTION | PRODUCT ATOMIC NUMBER | PRODUCT ELEMENT | MASS NUMBER | HALF-LIFE | DESCENDANT NUCLIDE(S) 1 | DESCENDANT NUCLIDE(S) 2 | HEATING 350° C. TARGET | HEATING 350° C. PRODUCT | HEATING 650° C. TARGET | HEATING 650° C. PRODUCT |
|---|---|---|---|---|---|---|---|---|---|---|---|---|---|---|
| 1 | 16 | S | 34 | p,n | 17 | Cl | 34 m | 31.99 m | | | Liq. | Gas | Gas | Gas |
| 2 | 16 | S | 34 | α,n | 18 | Ar | 37 | 35.01 d | | | Liq. | Gas | Gas | Gas |
| 3 | 31 | Ga | 69 | α,n | 33 | As | 72 | 26.0 h | | | Liq. | Sol. | Liq. | Gas |
| 4 | 31 | Ga | 69 | α,2n | 33 | As | 71 | 65.30 h | Ge-71 | | Liq. | Sol. | Liq. | Gas |
| 5 | 31 | Ga | 69 | α,3n | 33 | As | 70 | 52.6 m | | | Liq. | Sol. | Liq. | Gas |
| 6 | 31 | Ga | 69 | 7Li,d | 33 | As | 74 | 17.77 d | | | Liq. | Sol. | Liq. | Gas |
| 7 | 31 | Ga | 71 | α,n | 33 | As | 74 | 17.77 d | | | Liq. | Sol. | Liq. | Gas |
| 8 | 31 | Ga | 71 | α,2n | 33 | As | 73 | 80.30 d | | | Liq. | Sol. | Liq. | Gas |
| 9 | 31 | Ga | 71 | α,3n | 33 | As | 72 | 26.0 h | | | Liq. | Sol. | Liq. | Gas |
| 10 | 31 | Ga | 71 | 7Li,p | 33 | As | 77 | 38.79 h | | | Liq. | Sol. | Liq. | Gas |
| 11 | 31 | Ga | 71 | 7Li,d | 33 | As | 76 | 26.24 h | | | Liq. | Sol. | Liq. | Gas |
| 12 | 34 | Se | 74 | p,n | 35 | Br | 74 | 25.4 m | | | Liq. | Gas | Liq. | Gas |
| 13 | 34 | Se | 74 | α,n | 36 | Kr | 77 | 74.4 m | Br-77 | | Liq. | Gas | Liq. | Gas |
| 14 | 34 | Se | 74 | α,2n | 36 | Kr | 76 | 14.8 h | Br-76 | | Liq. | Gas | Liq. | Gas |
| 15 | 34 | Se | 74 | α,3n | 36 | Kr | 75 | 4.60 h | Br-75 | Se-75 | Liq. | Gas | Liq. | Gas |
| 16 | 34 | Se | 76 | p,n | 35 | Br | 76 | 16.1 h | | | Liq. | Gas | Liq. | Gas |
| 17 | 34 | Se | 76 | p,2n | 35 | Br | 75 | 96.7 m | Se-75 | | Liq. | Gas | Liq. | Gas |
| 18 | 34 | Se | 76 | p,3n | 35 | Br | 74 | 25.4 m | | | Liq. | Gas | Liq. | Gas |
| 19 | 34 | Se | 76 | α,n | 36 | Kr | 79 | 35.04 h | | | Liq. | Gas | Liq. | Gas |
| 20 | 34 | Se | 76 | α,3n | 36 | Kr | 77 | 74.4 h | Br-77 | | Liq. | Gas | Liq. | Gas |
| 21 | 34 | Se | 77 | p,n | 35 | Br | 77 | 57.04 h | | | Liq. | Gas | Liq. | Gas |
| 22 | 34 | Se | 77 | p,2n | 35 | Br | 76 | 16.1 h | | | Liq. | Gas | Liq. | Gas |
| 23 | 34 | Se | 77 | p,3n | 35 | Br | 75 | 96.7 m | Se-75 | | Liq. | Gas | Liq. | Gas |
| 24 | 34 | Se | 77 | α,2n | 36 | Kr | 79 | 35.04 h | | | Liq. | Gas | Liq. | Gas |
| 25 | 34 | Se | 78 | p,2n | 35 | Br | 77 | 57.04 h | | | Liq. | Gas | Liq. | Gas |
| 26 | 34 | Se | 78 | p,3n | 35 | Br | 76 | 16.1 h | | | Liq. | Gas | Liq. | Gas |
| 27 | 34 | Se | 78 | α,3n | 36 | Kr | 79 | 35.04 h | | | Liq. | Gas | Liq. | Gas |
| 28 | 34 | Se | 80 | p,n | 35 | Br | 80 | 17.68 m | | | Liq. | Gas | Liq. | Gas |
| 29 | 34 | Se | 80 | p,n | 35 | Br | 80 m | 4.42 h | | | Liq. | Gas | Liq. | Gas |
| 30 | 34 | Se | 80 | p,3n | 35 | Br | 78 | 6.45 m | | | Liq. | Gas | Liq. | Gas |

TABLE 2

| No. | TARGET ATOMIC NUMBER | TARGET ELEMENT | MASS NUMBER | NUCLEAR REACTION | PRODUCT ATOMIC NUMBER | PRODUCT ELEMENT | MASS NUMBER | HALF-LIFE | DESCENDANT NUCLIDE(S) 1 | DESCENDANT NUCLIDE(S) 2 | HEATING 350° C. TARGET | HEATING 350° C. PRODUCT | HEATING 650° C. TARGET | HEATING 650° C. PRODUCT |
|---|---|---|---|---|---|---|---|---|---|---|---|---|---|---|
| 31 | 34 | Se | 80 | α,n | 36 | Kr | 83 m | 1.83 h | | | Liq. | Gas | Liq. | Gas |
| 32 | 34 | Se | 82 | p,n | 35 | Br | 82 | 35.3 h | | | Liq. | Gas | Liq. | Gas |
| 33 | 34 | Se | 82 | p,3n | 35 | Br | 80 | 17.68 m | | | Liq. | Gas | Liq. | Gas |
| 34 | 34 | Se | 82 | p,3n | 35 | Br | 80 m | 4.42 h | | | Liq. | Gas | Liq. | Gas |
| 35 | 34 | Se | 82 | α,n | 36 | Kr | 85 | 10.74 y | | | Liq. | Gas | Liq. | Gas |
| 36 | 50 | Sn | 112 | 7Li,3n | 53 | I | 116 | 2.91 s | Te-116 | Sb-116 | Liq. | Gas | Liq. | Gas |
| 31 | 50 | Sn | 112 | 7Li,4n | 53 | I | 115 | 1.3 m | Te-115 | Sb-115 | Liq. | Gas | Liq. | Gas |
| 38 | 50 | Sn | 112 | 7Li,5n | 53 | I | 114 | 2.1 s | Te-114 | Sb-114 | Liq. | Gas | Liq. | Gas |
| 39 | 50 | Sn | 112 | 7Li,6n | 53 | I | 113 | 6.6 s | Te-113 | Sb-113 | Liq. | Gas | Liq. | Gas |
| 40 | 50 | Sn | 112 | 7Li,7n | 53 | I | 112 | 3.34 s | Te-112 | Sb-112 | Liq. | Gas | Liq. | Gas |
| 41 | 50 | Sn | 112 | 7Li,8n | 53 | I | 111 | 2.5 s | Te-111 | Sb-111 | Liq. | Gas | Liq. | Gas |
| 42 | 50 | Sn | 112 | 7Li,9n | 53 | I | 110 | 664 ms | Te-110 | Sb-110 | Liq. | Gas | Liq. | Gas |
| 43 | 50 | Sn | 114 | 7Li,3n | 53 | I | 118 | 13.7 m | Te-118 | | Liq. | Gas | Liq. | Gas |
| 44 | 50 | Sn | 114 | 7Li,4n | 53 | I | 117 | 2.22 m | Te-117 | Sb-117 | Liq. | Gas | Liq. | Gas |
| 45 | 50 | Sn | 114 | 7Li,5n | 53 | I | 116 | 2.91 s | Te-116 | Sb-116 | Liq. | Gas | Liq. | Gas |
| 46 | 50 | Sn | 114 | 7Li,6n | 53 | I | 115 | 1.3 m | Te-115 | Sb-115 | Liq. | Gas | Liq. | Gas |
| 47 | 50 | Sn | 114 | 7Li,7n | 53 | I | 114 | 2.1 s | Te-114 | Sb-114 | Liq. | Gas | Liq. | Gas |
| 48 | 50 | Sn | 114 | 7Li,8n | 53 | I | 113 | 6.6 s | Te-113 | Sb-113 | Liq. | Gas | Liq. | Gas |
| 49 | 50 | Sn | 114 | 7Li,9n | 53 | I | 112 | 3.34 s | Te-112 | Sb-112 | Liq. | Gas | Liq. | Gas |
| 50 | 50 | Sn | 114 | 7Li,6Li | 53 | I | 115 | 1.3 m | Te-115 | Sb-115 | Liq. | Gas | Liq. | Gas |
| 51 | 50 | Sn | 115 | 7Li,3n | 53 | I | 119 | 19.1 m | Te-119 | Sb-119 | Liq. | Gas | Liq. | Gas |
| 52 | 50 | Sn | 115 | 7Li,4n | 53 | I | 118 | 13.7 m | Te-118 | | Liq. | Gas | Liq. | Gas |
| 53 | 50 | Sn | 115 | 7Li,5n | 53 | I | 117 | 2.22 m | Te-117 | Sb-117 | Liq. | Gas | Liq. | Gas |
| 54 | 50 | Sn | 115 | 7Li,6n | 53 | I | 116 | 2.91 s | Te-116 | Sb-116 | Liq. | Gas | Liq. | Gas |

TABLE 2-continued

| No. | TARGET ATOMIC NUMBER | TARGET ELEMENT | TARGET MASS NUMBER | NUCLEAR REACTION | PRODUCT ATOMIC NUMBER | PRODUCT ELEMENT | PRODUCT MASS NUMBER | PRODUCT HALF-LIFE | DESCENDANT NUCLIDE(S) 1 | DESCENDANT NUCLIDE(S) 2 | HEATING TEMPERATURE 350° C. TARGET | HEATING TEMPERATURE 350° C. PRODUCT | HEATING TEMPERATURE 650° C. TARGET | HEATING TEMPERATURE 650° C. PRODUCT |
|---|---|---|---|---|---|---|---|---|---|---|---|---|---|---|
| 55 | 50 | Sn | 115 | 7Li,7n | 53 | I | 115 | 1.3 m | Te-115 | Sb-115 | Liq. | Gas | Liq. | Gas |
| 56 | 50 | Sn | 115 | 7Li,8n | 53 | I | 114 | 2.1 s | Te-114 | Sb-114 | Liq. | Gas | Liq. | Gas |
| 57 | 50 | Sn | 115 | 7Li,9n | 53 | I | 113 | 6.6 s | Te-113 | Sb-113 | Liq. | Gas | Liq. | Gas |
| 58 | 50 | Sn | 116 | 7Li,3n | 53 | I | 120 | 81.6 m | Sb-120 | | Liq. | Gas | Liq. | Gas |
| 59 | 50 | Sn | 116 | 7Li,3n | 53 | I | 120 m | 53 m | Sb-120 | | Liq. | Gas | Liq. | Gas |
| 60 | 50 | Sn | 116 | 7Li,4n | 53 | I | 119 | 19.1 m | Te-119 | Sb-119 | Liq. | Gas | Liq. | Gas |

TABLE 3

| No. | TARGET ATOMIC NUMBER | TARGET ELEMENT | TARGET MASS NUMBER | NUCLEAR REACTION | PRODUCT ATOMIC NUMBER | PRODUCT ELEMENT | PRODUCT MASS NUMBER | PRODUCT HALF-LIFE | DESCENDANT NUCLIDE(S) 1 | DESCENDANT NUCLIDE(S) 2 | HEATING TEMPERATURE 350° C. TARGET | HEATING TEMPERATURE 350° C. PRODUCT | HEATING TEMPERATURE 650° C. TARGET | HEATING TEMPERATURE 650° C. PRODUCT |
|---|---|---|---|---|---|---|---|---|---|---|---|---|---|---|
| 61 | 50 | Sn | 116 | 7Li,5n | 53 | I | 118 | 13.7 m | Te-118 | | Liq. | Gas | Liq. | Gas |
| 62 | 50 | Sn | 116 | 7Li,6n | 53 | I | 117 | 2.22 m | Te-117 | Sb-117 | Liq. | Gas | Liq. | Gas |
| 63 | 50 | Sn | 116 | 7Li,7n | 53 | I | 116 | 2.91 s | Te-116 | Sb-116 | Liq. | Gas | Liq. | Gas |
| 64 | 50 | Sn | 116 | 7Li,8n | 53 | I | 115 | 1.3 m | Te-115 | Sb-115 | Liq. | Gas | Liq. | Gas |
| 65 | 50 | Sn | 116 | 7Li,9n | 53 | I | 114 | 2.1 s | Te-114 | Sb-114 | Liq. | Gas | Liq. | Gas |
| 66 | 50 | Sn | 117 | 7Li,3n | 53 | I | 121 | 2.12 h | Te-121 | | Liq. | Gas | Liq. | Gas |
| 67 | 50 | Sn | 117 | 7Li,4n | 53 | I | 120 | 81.6 m | Sb-120 | | Liq. | Gas | Liq. | Gas |
| 68 | 50 | Sn | 117 | 7Li,4n | 53 | I | 120 m | 53 m | Sb-120 | | Liq. | Gas | Liq. | Gas |
| 69 | 50 | Sn | 117 | 7Li,5n | 53 | I | 119 | 19.1 m | Te-119 | Sb-119 | Liq. | Gas | Liq. | Gas |
| 70 | 50 | Sn | 117 | 7Li,6n | 53 | I | 118 | 13.7 m | Te-118 | | Liq. | Gas | Liq. | Gas |
| 71 | 50 | Sn | 117 | 7Li,7n | 53 | I | 117 | 2.22 m | Te-117 | Sb-117 | Liq. | Gas | Liq. | Gas |
| 72 | 50 | Sn | 117 | 7Li,8n | 53 | I | 116 | 2.91 s | Te-116 | Sb-116 | Liq. | Gas | Liq. | Gas |
| 73 | 50 | Sn | 117 | 7Li,9n | 53 | I | 115 | 1.3 m | Te-115 | Sb-115 | Liq. | Gas | Liq. | Gas |
| 74 | 50 | Sn | 118 | 7Li,4n | 53 | I | 121 | 2.12 h | Te-121 | | Liq. | Gas | Liq. | Gas |
| 75 | 50 | Sn | 118 | 7Li,5n | 53 | I | 120 | 81.6 m | Sb-120 | | Liq. | Gas | Liq. | Gas |
| 76 | 50 | Sn | 118 | 7Li,5n | 53 | I | 120 m | 53 m | Sb-120 | | Liq. | Gas | Liq. | Gas |
| 77 | 50 | Sn | 118 | 7Li,6n | 53 | I | 119 | 19.1 m | Te-119 | Sb-119 | Liq. | Gas | Liq. | Gas |
| 78 | 50 | Sn | 118 | 7Li,7n | 53 | I | 118 | 13.7 m | Te-118 | | Liq. | Gas | Liq. | Gas |
| 79 | 50 | Sn | 118 | 7Li,8n | 53 | I | 117 | 2.22 m | Te-117 | Sb-117 | Liq. | Gas | Liq. | Gas |
| 80 | 50 | Sn | 118 | 7Li,9n | 53 | I | 116 | 2.91 s | Te-116 | Sb-116 | Liq. | Gas | Liq. | Gas |
| 81 | 50 | Sn | 119 | 7Li,3n | 53 | I | 123 | 13.22 h | | | Liq. | Gas | Liq. | Gas |
| 82 | 50 | Sn | 119 | 7Li,5n | 53 | I | 121 | 2.12 h | Te-121 | | Liq. | Gas | Liq. | Gas |
| 83 | 50 | Sn | 119 | 7Li,6n | 53 | I | 120 | 81.6 m | Sb-120 | | Liq. | Gas | Liq. | Gas |
| 84 | 50 | Sn | 119 | 7Li,6n | 53 | I | 120 m | 53 m | Sb-120 | | Liq. | Gas | Liq. | Gas |
| 85 | 50 | Sn | 119 | 7Li,7n | 53 | I | 119 | 19.1 m | Te-119 | Sb-119 | Liq. | Gas | Liq. | Gas |
| 86 | 50 | Sn | 119 | 7Li,8n | 53 | I | 118 | 13.7 m | Te-118 | | Liq. | Gas | Liq. | Gas |
| 87 | 50 | Sn | 119 | 7Li,9n | 53 | I | 117 | 2.22 m | Te-117 | Sb-117 | Liq. | Gas | Liq. | Gas |
| 88 | 50 | Sn | 120 | 7Li,3n | 53 | I | 124 | 4.17 d | | | Liq. | Gas | Liq. | Gas |
| 89 | 50 | Sn | 120 | 7Li,4n | 53 | I | 123 | 13.22 h | | | Liq. | Gas | Liq. | Gas |
| 90 | 50 | Sn | 120 | 7Li,6n | 53 | I | 121 | 2.12 h | Te-121 | | Liq. | Gas | Liq. | Gas |

TABLE 4

| No. | TARGET ATOMIC NUMBER | TARGET ELEMENT | TARGET MASS NUMBER | NUCLEAR REACTION | PRODUCT ATOMIC NUMBER | PRODUCT ELEMENT | PRODUCT MASS NUMBER | PRODUCT HALF-LIFE | DESCENDANT NUCLIDE(S) 1 | DESCENDANT NUCLIDE(S) 2 | HEATING TEMPERATURE 350° C. TARGET | HEATING TEMPERATURE 350° C. PRODUCT | HEATING TEMPERATURE 650° C. TARGET | HEATING TEMPERATURE 650° C. PRODUCT |
|---|---|---|---|---|---|---|---|---|---|---|---|---|---|---|
| 91 | 50 | Sn | 120 | 7Li,7n | 53 | I | 120 | 81.6 m | Sb-120 | | Liq. | Gas | Liq. | Gas |
| 92 | 50 | Sn | 120 | 7Li,7n | 53 | I | 120 m | 53 m | Sb-120 | | Liq. | Gas | Liq. | Gas |

TABLE 4-continued

| No. | TARGET ATOMIC NUMBER | ELE-MENT | MASS NUMBER | NU-CLEAR REAC-TION | PRODUCT ATOMIC NUMBER | ELE-MENT | MASS NUMBER | HALF-LIFE | DE-SCEND-ANT NU-CLIDE(S) 1 | 2 | HEATING TEMPERATURE 350° C. TAR-GET | PRO-DUCT | 650° C. TAR-GET | PRO-DUCT |
|---|---|---|---|---|---|---|---|---|---|---|---|---|---|---|
| 93 | 50 | Sn | 120 | 7Li,8n | 53 | I | 119 | 19.1 m | Te-119 | Sb-119 | Liq. | Gas | Liq. | Gas |
| 94 | 50 | Sn | 120 | 7Li,9n | 53 | I | 118 | 13.7 m | Te-118 | | Liq. | Gas | Liq. | Gas |
| 95 | 50 | Sn | 122 | 7Li,3n | 53 | I | 126 | 12.93 d | | | Liq. | Gas | Liq. | Gas |
| 96 | 50 | Sn | 122 | 7Li,4n | 53 | I | 125 | 59.4 d | | | Liq. | Gas | Liq. | Gas |
| 97 | 50 | Sn | 122 | 7Li,5n | 53 | I | 124 | 4.17 d | | | Liq. | Gas | Liq. | Gas |
| 98 | 50 | Sn | 122 | 7Li,6n | 53 | I | 123 | 13.22 h | | | Liq. | Gas | Liq. | Gas |
| 99 | 50 | Sn | 122 | 7Li,8n | 53 | I | 121 | 2.12 h | Te-121 | | Liq. | Gas | Liq. | Gas |
| 100 | 50 | Sn | 122 | 7Li,9n | 53 | I | 120 | 81.6 m | Sb-120 | | Liq. | Gas | Liq. | Gas |
| 101 | 50 | Sn | 122 | 7Li,9n | 53 | I | 120 m | 53 m | Sb-120 | | Liq. | Gas | Liq. | Gas |
| 102 | 51 | Sb | 121 | α,n | 53 | I | 124 | 4.17 d | | | Sol. | Gas | Liq. | Gas |
| 103 | 51 | Sb | 121 | α,2n | 53 | I | 123 | 13.22 h | | | Sol. | Gas | Liq. | Gas |
| 104 | 51 | Sb | 121 | 7Li,3n | 54 | Xe | 125 | 16.9 h | | | Sol. | Gas | Liq. | Gas |
| 105 | 51 | Sb | 121 | 7Li,5n | 54 | Xe | 123 | 2.08 h | | | Sol. | Gas | Liq. | Gas |
| 106 | 51 | Sb | 121 | 7Li,6n | 54 | Xe | 122 | 20.1 h | | | Sol. | Gas | Liq. | Gas |
| 107 | 51 | Sb | 121 | 7Li,7n | 54 | Xe | 121 | 40.1 m | | | Sol. | Gas | Liq. | Gas |
| 108 | 51 | Sb | 121 | 7Li,8n | 54 | Xe | 120 | 40 m | | | Sol. | Gas | Liq. | Gas |
| 109 | 51 | Sb | 121 | 7Li,6n | 53 | I | 126 | 12.93 d | | | Sol. | Gas | Liq. | Gas |
| 110 | 51 | Sb | 123 | α,n | 53 | I | 126 | 12.93 d | | | Sol. | Gas | Liq. | Gas |
| 111 | 51 | Sb | 123 | α,2n | 53 | I | 125 | 59.4 d | | | Sol. | Gas | Liq. | Gas |
| 112 | 51 | Sb | 123 | α,3n | 53 | I | 124 | 4.17 d | | | Sol. | Gas | Liq. | Gas |
| 113 | 51 | Sb | 123 | 7Li,3n | 54 | Xe | 127 | 36.4 d | | | Sol. | Gas | Liq. | Gas |
| 114 | 51 | Sb | 123 | 7Li,5n | 54 | Xe | 125 | 16.9 h | | | Sol. | Gas | Liq. | Gas |
| 115 | 51 | Sb | 123 | 7Li,7n | 54 | Xe | 123 | 2.08 h | | | Sol. | Gas | Liq. | Gas |
| 116 | 51 | Sb | 123 | 7Li,8n | 54 | Xe | 122 | 20.1 h | | | Sol. | Gas | Liq. | Gas |
| 117 | 51 | Sb | 123 | 7Li,9n | 54 | Xe | 121 | 40.1 m | | | Sol. | Gas | Liq. | Gas |
| 118 | 51 | Sb | 123 | 7Li,p | 53 | I | 129 | 1.57e7 y | | | Sol. | Gas | Liq. | Gas |
| 119 | 51 | Sb | 123 | 7Li,d | 53 | I | 128 | 25.0 m | | | Sol. | Gas | Liq. | Gas |
| 120 | 52 | Te | 120 | p,n | 53 | I | 120 | 81.6 m | Sb-120 | | Sol. | Gas | Liq. | Gas |

TABLE 5

| No. | TARGET ATOMIC NUMBER | ELE-MENT | MASS NUMBER | NU-CLEAR REAC-TION | PRODUCT ATOMIC NUMBER | ELE-MENT | MASS NUMBER | HALF-LIFE | DE-SCEND-ANT NU-CLIDE(S) 1 | 2 | HEATING TEMPERATURE 350° C. TAR-GET | PRO-DUCT | 650° C. TAR-GET | PRO-DUCT |
|---|---|---|---|---|---|---|---|---|---|---|---|---|---|---|
| 121 | 52 | Te | 120 | p,n | 53 | I | 120 m | 53 m | Sb-120 | | Sol. | Gas | Liq. | Gas |
| 122 | 52 | Te | 120 | p,2n | 53 | I | 119 | 19.1 m | Te-119 | Sb-119 | Sol. | Gas | Liq. | Gas |
| 123 | 52 | Te | 120 | p,3n | 53 | I | 118 | 13.7 m | Te-118 | | Sol. | Gas | Liq. | Gas |
| 124 | 52 | Te | 120 | α,n | 54 | Xe | 123 | 2.08 h | | | Sol. | Gas | Liq. | Gas |
| 125 | 52 | Te | 120 | α,2n | 54 | Xe | 122 | 20.1 h | | | Sol. | Gas | Liq. | Gas |
| 126 | 52 | Te | 120 | α,3n | 54 | Xe | 121 | 40.1 m | | | Sol. | Gas | Liq. | Gas |
| 127 | 52 | Te | 122 | p,2n | 53 | I | 121 | 2.12 h | Te-121 | | Sol. | Gas | Liq. | Gas |
| 128 | 52 | Te | 122 | p,3n | 53 | I | 120 | 81.6 m | Sb-120 | | Sol. | Gas | Liq. | Gas |
| 129 | 52 | Te | 122 | p,3n | 53 | I | 120 m | 53 m | Sb-120 | | Sol. | Gas | Liq. | Gas |
| 130 | 52 | Te | 122 | α,n | 54 | Xe | 125 | 16.9 h | | | Sol. | Gas | Liq. | Gas |
| 131 | 52 | Te | 122 | α,3n | 54 | Xe | 123 | 2.08 h | | | Sol. | Gas | Liq. | Gas |
| 132 | 52 | Te | 124 | p,n | 53 | I | 124 | 4.17 d | | | Sol. | Gas | Liq. | Gas |
| 133 | 52 | Te | 124 | p,2n | 53 | I | 123 | 13.22 h | | | Sol. | Gas | Liq. | Gas |
| 134 | 52 | Te | 124 | α,n | 54 | Xe | 127 | 36.4 d | | | Sol. | Gas | Liq. | Gas |

TABLE 5-continued

| No. | TARGET ATOMIC NUMBER | TARGET ELEMENT | TARGET MASS NUMBER | NUCLEAR REACTION | PRODUCT ATOMIC NUMBER | PRODUCT ELEMENT | PRODUCT MASS NUMBER | HALF-LIFE | DESCENDANT NUCLIDE(S) 1 | DESCENDANT NUCLIDE(S) 2 | HEATING TEMPERATURE 350° C. TARGET | HEATING TEMPERATURE 350° C. PRODUCT | HEATING TEMPERATURE 650° C. TARGET | HEATING TEMPERATURE 650° C. PRODUCT |
|---|---|---|---|---|---|---|---|---|---|---|---|---|---|---|
| 135 | 52 | Te | 124 | α,3n | 54 | Xe | 125 | 16.9 h | | | Sol. | Gas | Liq. | Gas |
| 136 | 52 | Te | 125 | p,n | 53 | I | 125 | 59.4 d | | | Sol. | Gas | Liq. | Gas |
| 137 | 52 | Te | 125 | p,2n | 53 | I | 124 | 4.17 d | | | Sol. | Gas | Liq. | Gas |
| 138 | 52 | Te | 125 | p,3n | 53 | I | 123 | 13.22 h | | | Sol. | Gas | Liq. | Gas |
| 139 | 52 | Te | 125 | α,2n | 54 | Xe | 127 | 36.4 d | | | Sol. | Gas | Liq. | Gas |
| 140 | 52 | Te | 126 | p,n | 53 | I | 126 | 12.93 d | | | Sol. | Gas | Liq. | Gas |
| 141 | 52 | Te | 126 | p,2n | 53 | I | 125 | 59.4 d | | | Sol. | Gas | Liq. | Gas |
| 142 | 52 | Te | 126 | p,3n | 53 | I | 124 | 4.17 d | | | Sol. | Gas | Liq. | Gas |
| 143 | 52 | Te | 126 | α,n | 54 | Xe | 129 m | 8.88 d | | | Sol. | Gas | Liq. | Gas |
| 144 | 52 | Te | 126 | α,3n | 54 | Xe | 127 | 36.4 d | | | Sol. | Gas | Liq. | Gas |
| 145 | 52 | Te | 128 | p,n | 53 | I | 123 | 25.0 m | | | Sol. | Gas | Liq. | Gas |
| 146 | 52 | Te | 128 | p,3n | 53 | I | 126 | 12.93 d | | | Sol. | Gas | Liq. | Gas |
| 147 | 52 | Te | 128 | α,n | 54 | Xe | 131 m | 11.84 d | | | Sol. | Gas | Liq. | Gas |
| 148 | 52 | Te | 128 | α,3n | 54 | Xe | 129 m | 8.88 d | | | Sol. | Gas | Liq. | Gas |
| 149 | 52 | Te | 130 | p,n | 53 | I | 130 | 12.36 h | | | Sol. | Gas | Liq. | Gas |
| 150 | 52 | Te | 130 | p,2n | 53 | I | 129 | 1.57e7 y | | | Sol. | Gas | Liq. | Gas |

TABLE 6

| No. | TARGET ATOMIC NUMBER | TARGET ELEMENT | TARGET MASS NUMBER | NUCLEAR REACTION | PRODUCT ATOMIC NUMBER | PRODUCT ELEMENT | PRODUCT MASS NUMBER | HALF-LIFE | DESCENDANT NUCLIDE(S) 1 | DESCENDANT NUCLIDE(S) 2 | HEATING TEMPERATURE 350° C. TARGET | HEATING TEMPERATURE 350° C. PRODUCT | HEATING TEMPERATURE 650° C. TARGET | HEATING TEMPERATURE 650° C. PRODUCT |
|---|---|---|---|---|---|---|---|---|---|---|---|---|---|---|
| 151 | 52 | Te | 130 | p,3n | 53 | I | 128 | 25.0 m | | | Sol. | Gas | Liq. | Gas |
| 152 | 52 | Te | 130 | α,n | 54 | Xe | 133 | 5.25 d | | | Sol. | Gas | Liq. | Gas |
| 153 | 52 | Te | 130 | α,n | 54 | Xe | 133 m | 2.2 d | | | Sol. | Gas | Liq. | Gas |
| 154 | 82 | Pb | 204 | 7Li,3n | 85 | At | 208 | 1.63 h | * | | Liq. | Gas | Liq. | Gas |
| 155 | 82 | Pb | 204 | 7Li,4n | 85 | At | 207 | 1.81 h | * | | Liq. | Gas | Liq. | Gas |
| 156 | 82 | Pb | 204 | 7Li,5n | 85 | At | 206 | 30.6 m | * | | Liq. | Gas | Liq. | Gas |
| 157 | 82 | Pb | 204 | 7Li,6n | 85 | At | 205 | 26.9 m | * | | Liq. | Gas | Liq. | Gas |
| 158 | 82 | Pb | 204 | 7Li,7n | 85 | At | 204 | 9.12 m | * | | Liq. | Gas | Liq. | Gas |
| 159 | 82 | Pb | 204 | 7Li,8n | 85 | At | 203 | 7.4 m | * | | Liq. | Gas | Liq. | Gas |
| 160 | 82 | Pb | 204 | 7Li,p | 84 | Po | 210 | 138.4 d | * | | Liq. | Gas | Liq. | Gas |
| 161 | 32 | Pb | 204 | 7Li,d | 84 | Po | 209 | 124 y | * | | Liq. | Gas | Liq. | Gas |
| 162 | 82 | Pb | 206 | 7Li,3n | 85 | At | 210 | 8.1 h | * | | Liq. | Gas | Liq. | Gas |
| 163 | 82 | Pb | 206 | 7Li,4n | 85 | At | 209 | 5.42 h | * | | Liq. | Gas | Liq. | Gas |
| 164 | 82 | Pb | 206 | 7Li,5n | 85 | At | 208 | 1.63 h | * | | Liq. | Gas | Liq. | Gas |
| 165 | 82 | Pb | 206 | 7Li,6n | 85 | At | 207 | 1.81 h | * | | Liq. | Gas | Liq. | Gas |
| 166 | 32 | Pb | 206 | 7Li,7n | 85 | At | 206 | 30.6 m | * | | Liq. | Gas | Liq. | Gas |
| 167 | 82 | Pb | 206 | 7Li,8n | 85 | At | 205 | 26.9 m | * | | Liq. | Gas | Liq. | Gas |
| 168 | 82 | Pb | 206 | 7Li,9n | 85 | At | 204 | 9.12 m | * | | Liq. | Gas | Liq. | Gas |
| 169 | 82 | Pb | 207 | 7Li,3n | 85 | At | 211 | 7.214 h | * | | Liq. | Gas | Liq. | Gas |
| 170 | 82 | Pb | 207 | 7Li,4n | 85 | At | 210 | 8.1 h | * | | Liq. | Gas | Liq. | Gas |
| 171 | 82 | Pb | 207 | 7Li,5n | 85 | At | 209 | 5.42 h | * | | Liq. | Gas | Liq. | Gas |
| 172 | 82 | Pb | 207 | 7Li,6n | 85 | At | 208 | 1.63 h | * | | Liq. | Gas | Liq. | Gas |
| 173 | 82 | Pb | 207 | 7Li,7n | 85 | At | 207 | 1.81 h | * | | Liq. | Gas | Liq. | Gas |
| 174 | 82 | Pb | 207 | 7Li,8n | 85 | At | 206 | 30.6 m | * | | Liq. | Gas | Liq. | Gas |
| 175 | 32 | Pb | 207 | 7Li,9n | 85 | At | 205 | 26.9 m | * | | Liq. | Gas | Liq. | Gas |
| 176 | 82 | Pb | 208 | 7Li,4n | 85 | At | 211 | 7.214 h | * | | Liq. | Gas | Liq. | Gas |
| 177 | 82 | Pb | 208 | 7Li,5n | 85 | At | 210 | 8.1 h | * | | Liq. | Gas | Liq. | Gas |
| 178 | 82 | Pb | 208 | 7Li,6n | 85 | At | 209 | 5.42 h | * | | Liq. | Gas | Liq. | Gas |
| 179 | 82 | Pb | 208 | 7Li,7n | 85 | At | 208 | 1.63 h | * | | Liq. | Gas | Liq. | Gas |
| 180 | 82 | Pb | 208 | 7Li,8n | 85 | At | 207 | 1.81 h | * | | Liq. | Gas | Liq. | Gas |

TABLE 7

| No. | TARGET ATOMIC NUMBER | TARGET ELEMENT | NUCLEAR MASS NUMBER | NUCLEAR REACTION | PRODUCT ATOMIC NUMBER | PRODUCT ELEMENT | PRODUCT MASS NUMBER | PRODUCT HALF-LIFE | DESCENDANT NUCLIDE(S) 1 | DESCENDANT NUCLIDE(S) 2 | HEATING TEMPERATURE 350° C. TARGET | HEATING TEMPERATURE 350° C. PRODUCT | HEATING TEMPERATURE 650° C. TARGET | HEATING TEMPERATURE 650° C. PRODUCT |
|---|---|---|---|---|---|---|---|---|---|---|---|---|---|---|
| 181 | 82 | Pb | 208 | 7Li,9n | 85 | At | 206 | 30.6 m | * | | Liq. | Gas | Liq. | Gas |
| 182 | 83 | Bi | 209 | α,2n | 85 | At | 211 | 7.214 h | * | | Liq. | Gas | Liq. | Gas |
| 183 | 83 | Bi | 209 | α,3n | 85 | At | 210 | 8.1 h | * | | Liq. | Gas | Liq. | Gas |
| 184 | 83 | Bi | 209 | 7Li,3n | 86 | Rn | 213 | 19.5 ms | * | | Liq. | Gas | Liq. | Gas |
| 185 | 33 | Bi | 209 | 7Li,4n | 86 | Rn | 212 | 23.9 m | * | | Liq. | Gas | Liq. | Gas |
| 186 | 83 | Bi | 209 | 7Li,5n | 86 | Rn | 211 | 14.6 h | * | | Liq. | Gas | Liq. | Gas |
| 187 | 83 | Bi | 209 | 7Li,6n | 86 | Rn | 210 | 2.4 h | * | | Liq. | Gas | Liq. | Gas |
| 188 | 83 | Bi | 209 | 7Li,7n | 86 | Rn | 209 | 28.8 m | * | | Liq. | Gas | Liq. | Gas |
| 189 | 83 | Bi | 209 | 7Li,8n | 86 | Rn | 208 | 24.3 m | * | | Liq. | Gas | Liq. | Gas |
| 190 | 83 | Bi | 209 | 7Li,9n | 86 | Rn | 207 | 9.25 m | * | | Liq. | Gas | Liq. | Gas |

In each of the aforementioned tables, the description at the column labeled as "target" exemplarily presents elements which can be employed as target substances in the aforementioned embodiment and its modification, and as described in the tables, examples of those include sulfur (S), gallium (Ga), selenium (Se), tin (Sn), antimony (Sb), tellurium (Te), lead (Pb) and bismuth (Bi).

Moreover, in each of the aforementioned tables, the description at the column labeled as "nuclear reaction" exemplarily presents types of nuclear reactions with radiation beams irradiated on target substances in the aforementioned embodiment and its modification, and as described in the tables, examples of those include α-reaction using α-particles, p-reaction using protons, and nuclear reaction using lithium. At the column of the nuclear reaction, the left side of commas (,) represents ones which enter target substances, and the right side of the commas (,) represents ones which are emitted from the target substances.

Moreover, in each of the aforementioned tables, the description at the column labeled as "descendant nuclide(s)" exemplarily presents nuclide(s) generated through radioactive decay of products. As exemplarily presented in each of the aforementioned tables, germanium (Ge), bromine (Br) and the like are exemplarily presented as the descendant nuclide(s), and asterisks (*) are displayed for ones in which various kinds of descendant nuclides are generated not to be contained in the description column of the table.

Moreover, in each of the aforementioned tables, the description at the "target" column and at the "product" column in the column labeled as "heating temperature" presents the states of the substances, "Sol" represents being solid, "Liq" represents being liquid, and "Gas" represents being gas.

By applying the combinations of the targets and the nuclear reactions presented in the aforementioned tables to the aforementioned embodiment and its modification, as presented at the columns of "product" in the tables, various radioisotopes can be generated. Further, in each of the aforementioned tables, a target is a substance having a higher temperature at which it is gasified under a pressure in irradiating a radiation beam than a temperature at which a radioisotope as the product is gasified under the same pressure. Therefore, in the aforementioned embodiment and its modification, by adjusting the temperature of the target substance so as to be within a temperature range not less than the temperature at which the radioisotope is gasified under the same pressure and less than the temperature at which the target substance is gasified under the same pressure, the target substance is not gasified but the radioisotope is gasified, and the radioisotope can be extracted from the gas in the trap 130. Notably, "gasification" stated in this application is that a substance is in the state of gas, and, for example, is a concept including the state where it is transferred to the gas phase by exceeding its boiling point or its sublimation point. Therefore, the "temperature at which the target substance is gasified under the same pressure" mentioned above can be replaced by the "boiling point or the sublimation point at which the target substance is vaporized under the same pressure".

For example, with the combination of No. 1 in the table, while the boiling point of sulfur (S) as a target substance at ambient pressure is approximately 444° C., the boiling point of chlorine (Cl) as the product at ambient pressure is approximately −34° C., which is lower than that of sulfur (S), therefore, as presented at the "heating temperature" column in the table, when the radiation beam is irradiated on the target in the state where the temperature in the crucible 102 is 350° C., chlorine (Cl) as the product is exclusively vaporized in the crucible 102 while sulfur (S) as the target substance maintains the state of liquid, and chlorine (Cl) vaporized in the crucible 102 is extracted through its condensation in the trap 130.

Moreover, for example, with the combination of No. 3 or No. 7 in the table, while the boiling point of gallium (Ga) as a target substance at ambient pressure is approximately 2400° C., the boiling point of arsenic (As) as the product at ambient pressure is approximately 613° C., which is lower than that of gallium (Ga), therefore, as presented at the "heating temperature" column in the table, when the radiation beam is irradiated on the target in the state where the temperature in the crucible 102 is 650° C., arsenic (As) as the product is exclusively vaporized in the crucible 102 while gallium (Ga) as the target substance maintains the state of liquid, and arsenic (As) vaporized in the crucible 102 is extracted through its condensation in the trap 130.

Moreover, for example, with the combination of No. 12, No. 16 or No. 22 in the table, while the boiling point of selenium (Se) as a target substance at ambient pressure is approximately 684° C., the boiling point of bromine (Br) as the product at ambient pressure is approximately 58° C., which is lower than that of selenium (Se), therefore, as presented at the "heating temperature" column in the table, when the radiation beam is irradiated on the target in the state where the temperature in the crucible 102 is 350° C. or 650° C., bromine (Br) as the product is exclusively vaporized in the crucible 102 while selenium (Se) as the target substance maintains the state of liquid, and bromine (Br) vaporized in the crucible 102 is extracted through its condensation in the trap 130.

Moreover, for example, with the combination of No. 102 or No. 112 in the table, while the boiling point of antimony (Sb) as a target substance at ambient pressure is approximately 1587° C., the boiling point of iodine (I) at the product at ambient pressure is approximately 148° C., which is lower than that of antimony (Sb), therefore, as presented at the "heating temperature" column in the table, when the radiation beam is irradiated on the target in the state where the temperature in the crucible 102 is 350° C. or 650° C., iodine (I) as the product is exclusively vaporized in the crucible 102 while antimony (Sb) as the target substance maintains the state of solid or liquid, and iodine (I) vaporized in the crucible 102 is extracted through its condensation in the trap 130.

Moreover, for example, with the combination of No. 186 in the table, while the boiling point of bismuth (Bi) as a target substance at ambient pressure is approximately 1564° C., the boiling point of radon (Rn) as the product at ambient pressure is approximately −62° C., which is lower than that of bismuth (Bi), therefore, as presented at the "heating temperature" column in the table, when the radiation beam is irradiated on the target in the state where the temperature in the crucible 102 is 350° C. or 650° C., radon (Rn) as the product is exclusively vaporized in the crucible 102 while bismuth (Bi) as the target substance maintains the state of solid or liquid, and radon (Rn) vaporized in the crucible 102 is extracted through its condensation in the trap 130.

Notably, while at the "heating temperature" column in each of the aforementioned tables, the two cases of temperatures of 350° C. and 650° C. are exemplarily presented, there is not limited to any of 350° C. and 650° C. the temperature in the crucible 102 in the case where the combinations of the targets and the nuclear reactions presented in the aforementioned tables are to be implemented in the aforementioned embodiment and its modification. Namely, the temperature of the target substance in the crucible 102 in the case where the combinations of the targets and the nuclear reactions presented in the aforementioned tables are to be implemented in the aforementioned embodiment and its modification can be any temperature within a temperature range not less than a temperature at which the product is gasified under a pressure in the crucible 102 and less than a temperature at which the target substance is gasified under the same pressure. For example, with the combination of No. 1 in the table, while the boiling point of sulfur (S) as a target substance at ambient pressure is approximately 444° C., the boiling point of chlorine (Cl) as the product at ambient pressure is approximately −34° C., which is lower than that of sulfur (S). Therefore, assuming that the interior of the crucible 102 is at ambient pressure, when the temperature of sulfur (S) in the crucible 102 is within a range from approximately −30° C. to approximately 440° C., chlorine (Cl) as the product can be exclusively vaporized in the crucible 102 without sulfur (S) as the target substance gasified to extract chlorine (Cl) vaporized in the crucible 102 through its condensation in the trap 130.

Moreover, while there are described, at the "target" column in each of the aforementioned tables, the names of elements as the targets alone, the crucible 102 is sufficient to contain a substance as a target as presented at the "target" column in each of the tables, there may be employed the state where two or more kinds of target substances are put therein, or there may be employed the state where a substance other than the target is put therein along with the target substance.

Notably, when two or more kinds of substances are put in the crucible 102 together to form an alloy, the melting point thereof is different from that in the case where each substance exists as a simple substance. For example, the melting point of an alloy prepared from bismuth (Bi) and tin (Sn) in the ratio of 58:42 is 138° C., at ambient pressure, which is lower than 271° C. as the melting point of bismuth (Bi) and 232° C. as the melting point of tin (Sn). Nevertheless, the boiling point of a product obtained by irradiating a radiation beam on bismuth (Bi) and the boiling point of a product obtained by irradiating the radiation beam on tin (Sn) themselves are not relevant to whether or not they are in the state of an alloy, and hence, each product can be selectively extracted with the trap 130 by adjusting the temperature in the crucible 102 to be appropriate.

Each of the aforementioned products can be used for medical diagnosis and treatment, and in addition, can also be used for various applications, other than medical purposes, such as quality control of farm products and industrial products, such, for example, as purposes of tracers with which the states of plants are observed such as transfers of substances from soil into the plants, and purposes of agents with which the states of industrial products are examined on their surface processing.

DESCRIPTION OF THE REFERENCE NUMERALS AND SYMBOLS

100 Radioisotope producing apparatus
102 Crucible
104 Heater
106 Jacket
110 Beam port
112 Beam window
114 Beam window
122 Inlet
124 Outlet
130 Trap
200 Radioisotope producing apparatus
202 Crucible
204 Heater
208 Nozzle
210 Beam port
212 Beam window
214 Beam window
222 Inlet
224 Outlet
230 Trap
240 Pump
250 Heat exchanger

The invention claimed is:

1. A method of producing a radioisotope, the method comprising:
    generating a radioisotope by irradiating a liquid target substance with a radiation beam in a hermetically sealed container housing the target substance;
    transferring the generated radioisotope from the liquid target to a gas phase; and
    extracting the transferred radioisotope from the gas phase by cooling in an extracting unit hermetically connected to the container by a pipe to allow gas to pass from the container to the extracting unit, wherein a temperature of the target substance is adjusted to be within a temperature range not less than a temperature at which the radioisotope is gasified under a pressure and less than a temperature at which the target substance is gasified under the pressure in the extracting unit, and wherein the pressure at which the radioisotope is gasified is controlled by regulating an amount of gas discharged at an outlet from the container to the extracting unit.

2. The method according to claim 1, comprising cooling the radioisotope to 4° C. or less in the extracting unit.

3. The method according to claim 1, comprising cooling the radioisotope in the extracting unit with at least one of cooling water, acetone-dry ice, and liquid nitrogen.

4. The method according to claim 1, comprising heating the target substance in the container before or during irradiating the target substance.

5. The method according to claim 1, wherein at least part of the target substance is solid during irradiation of the target substance in the container.

6. The method according to claim 1, wherein the target substance has a higher temperature at which the substance is gasified under a pressure in the container during irradiation than a temperature at which the radioisotope is gasified under the pressure.

7. The method according to claim 1, comprising cooling the target substance in the container by introducing cooling material into a jacket arranged around the container.

8. The method according to claim 1, wherein a cooling means circulates the target substance in the container into and out of the container.

9. The method according to claim 1, comprising maintaining a temperature of the target substance constant in the container by convection.

10. The method according to claim 1, wherein the radioisotope is a group 17 element or a group 18 element.

11. The method according to claim 10, wherein the element includes at least one of 209At, 210At, 211At, 34mCl, 75Br, 76Br, 77Br, 82Br, 123I, 124I, 125I, 126I, 133Xe, and 211Rn.

12. The method according to claim 10, wherein the target substance is two or more kinds of target substance.

13. An apparatus for producing a radioisotope, the radioisotope producing apparatus comprising:
a hermetically sealed container that houses a liquid target substance;
a beam introducing portion that irradiates the target substance in the container with a radiation beam to generate a radioisotope;
means for transferring the generated radioisotope from the liquid target to a gas phase; and
an extracting unit hermetically connected to the container by a pipe to pass gas from the container to the extracting unit, wherein the extracting unit extracts the transferred radioisotope from the gas phase by cooling,
wherein a temperature of the target substance is adjustable to be within a temperature ramie not less than a temperature at which the radioisotope is gasified under a pressure and less than a temperature at which the target substance is gasified under the pressure in the extracting unit, and wherein the pressure at which the radioisotope is gasified is controllable by regulating an amount of gas discharged at an outlet from the container to the extracting unit.

14. The apparatus according to claim 13, wherein the extracting unit is a cooling trap.

15. The apparatus according to claim 13, comprising a heating unit that heats the container.

16. The apparatus according to claim 13, comprising cooling means for cooling the target substance in the container.

17. The apparatus according to claim 16, wherein the cooling means cools the target substance in the container by introducing the cooling material into a jacket arranged around the container.

18. The apparatus according to claim 16, wherein the cooling means circulates the target substance in the container into and out of the container.

19. The apparatus according to claim 16, wherein the target substance in the container is maintained at a constant temperature by convection.

* * * * *

UNITED STATES PATENT AND TRADEMARK OFFICE
CERTIFICATE OF CORRECTION

PATENT NO. : 11,276,506 B2
APPLICATION NO. : 16/649685
DATED : March 15, 2022
INVENTOR(S) : Noriko Ishioka et al.

It is certified that error appears in the above-identified patent and that said Letters Patent is hereby corrected as shown below:

In the Claims

At Column 22, Line 15, "ramie" should be -- range --.

Signed and Sealed this
Twelfth Day of July, 2022

Katherine Kelly Vidal
*Director of the United States Patent and Trademark Office*